(12) United States Patent
Umebayashi

(10) Patent No.: US 7,069,777 B2
(45) Date of Patent: Jul. 4, 2006

(54) METHOD, DEVICE, AND SYSTEM FOR MEASURING LOAD ON A SPRING

(75) Inventor: Akira Umebayashi, Kanagawa (JP)

(73) Assignee: NHK Spring Co., Ltd., Kanagawa (JP)

( * ) Notice: Subject to any disclaimer, the term of this patent is extended or adjusted under 35 U.S.C. 154(b) by 77 days.

(21) Appl. No.: 10/854,806

(22) Filed: May 27, 2004

(65) Prior Publication Data

US 2004/0261515 A1   Dec. 30, 2004

(30) Foreign Application Priority Data

May 27, 2003   (JP)   ............................. 2003-149720

(51) Int. Cl.
*G01L 1/04*   (2006.01)
(52) U.S. Cl. ...................................................... 73/161
(58) Field of Classification Search .................... 73/161
See application file for complete search history.

(56) References Cited

U.S. PATENT DOCUMENTS 5,940,251 A * 8/1999 Giere et al. ............... 360/244.9

2002/0088922 A1 * 7/2002 Schmitz et al. ........... 250/206.1

FOREIGN PATENT DOCUMENTS

| JP | 6-44760    | 2/1994  |
| JP | 7-130116   | 5/1995  |
| JP | 9-257648   | 10/1997 |
| JP | 10-213495  | 8/1998  |
| JP | 10-228742  | 8/1998  |
| JP | 2000-28489 | 1/2000  |

* cited by examiner

*Primary Examiner*—Edward Lefkowitz
*Assistant Examiner*—Linda P. Field
(74) *Attorney, Agent, or Firm*—Armstrong, Kratz, Quintos, Hanson & Brooks, LLP

(57) ABSTRACT

A spring has a fixed end and a free end. A specific portion of the free end is elevated from the fixed end, and a load measuring device that measures the load on the spring is arranged so as to make a physical contact with the free end. An elevation is measured from the fixed end of a specific portion of the load measuring device where the free end and the load measuring device make the physical contact with each other. It is determined whether the elevation measured is equal to a specific elevation and the load on the spring is measured with the load measuring device when the elevation measured is equal to a specific elevation.

23 Claims, 10 Drawing Sheets

METHOD, DEVICE, AND SYSTEM FOR MEASURING LOAD ON A SPRING

BACKGROUND OF THE INVENTION

1) Field of the Invention

The present invention relates to a technology for measuring load on a spring. More specifically, the present invention relates to technology for measuring the load on a leaf spring (suspension) that supports the magnetic head in a hard disk drive (HDD).

2) Description of the Related Art

In many cases it is necessary to measure the load on a spring. For example, it is necessary to measure the load on a suspension, which supports the magnetic head in the HDD.

In accordance with dramatic improvement in a recording density of the HDD, it has become necessary to accurately manufacture the suspension. An amount levitation of the magnetic head at the time of recording and reproduction is depends on how much load is there on the suspension in a stationary state. Consequently, a head load of the suspension significantly affects a levitation posture and a levitation characteristic of the magnetic head. Therefore, head load of each suspension is measured when manufacturing the suspension.

FIG. 7 is a schematic for explaining a relation between a suspension 200 a magnetic disk 21. It is assumed here that the magnetic disk 21 is not rotating. The suspension 200 includes a support 24 that supports a base plate 201, a load beam 203 that is attached to the base plate 201 via a leaf spring section 202. A flexure 209 is attached to the load beam 203.

A slider 210 is attached to an upper surface of the flexure 209. The slider 210 slides with respect to a surface of the magnetic disk 21. A magnetic read/write head (not shown) is housed inside the slider 210. A sliding surface of the magnetic head opposed to the magnetic disk 21 is the slider 210. A dimple 28a is provided at a tip of the load beam 203 and it is in contact with the flexure 209. The dimple 208a serves as a rotation fulcrum for the slider 210.

The load beam 203 is elastically supported by the leaf sprint section 202. Therefore, when the magnetic disk 21 is not rotating, the slider 210 is pressed against the magnetic disk 21 due to the force of the leaf spring 202. The contact load, when the magnetic disk 21 is not rotating, with which the slider 210 is pressed against the magnetic disk 21 will be called as the head load.

When the magnetic disk 21 rotates, the slider 210 is pushed away from the magnetic disk 21 because of an airflow that is generated because of the rotation of the magnetic disk 21. In other words, the slider 210 levitates below (or above) the magnetic disk 21. Recording and/or reproduction of information from/in the magnetic disk 21 is performed in this manner. The amount of levitation depends on the buoyant force and a force caused by the bending of the suspension. In general, this amount of levitation is several nanometers to several tens nanometers.

The head load has been conventionally measured by a method as described below. This method is disclosed, for example, in Japanese Patent Application Laid-Open Publication No. H6-44760.

Note that, in an example described below, an object of measurement of the heat load is the suspension 200 not yet mounted with the slider 210. When the suspension 200 mounted with the slider 210 is an object of measurement, it is possible to measure the head load with the same method except that only a thickness (Z210 in FIG. 8) of the slider 210 has to be taken into account.

In FIG. 8, reference numeral 200a denotes the suspension 200 at the time when it is free (no load state). Reference numeral 200b denotes the suspension 200 at the time when the slider 210 is in contact with the magnetic disk 21 at the time of rotation stop (the same state as FIG. 7). A load given to the magnetic disk 21 by the suspension 200b via the slider 210 is the head load.

Reference sign Zf denotes a height of a flexure 209a of the suspension 200a at the time when it is free from a reference plane 25a of the fixed support 24. Reference sign Z21 denotes a height of a lower surface of the magnetic disk 21 (a surface in contact with the magnetic disk 21) from the reference plane 25a. Reference sign Zh denotes a height of a flexure 209b of the suspension 200b, which presses the slider 210 against the magnetic disk 21 at the time of rotation stop, from the reference plane 25a. The height Z21 of the lower surface of the magnetic disk 21 is (Zh+Z210).

Therefore, in measuring the head load of the suspension 200, as shown in FIGS. 8 and 9, in a state in which a load probe 310 of a load cell 300 is in contact with the flexure 209, the load cell 300 only has to be lowered to depress the flexure 209 to a position of the height Zh and measure a load (reaction) from the flexure 209 in that state with the load cell 300. In the following description, a more specific method of measuring a head load will be explained with reference to FIG. 10:

(1) first, prepare a suspension 200M (master workpiece), a load of which is known in advance;

(2) nip the master workpiece 200M with a workpiece clamp 400 and press the master workpiece 200M upward to fix it on a reference plane 401;

(3) move a load cell 420 upward with a vertical movement unit 410 such as an air cylinder to bring a load probe 425 of the load cell 420 into contact with the master workpiece 200M;

(4) move up and down an ascending-end stopper 430 to adjust a height of the load cell 420 while monitoring a load outputted by the load cell 420, and fix the ascending-end stopper 430 at a position where the load outputted by the load cell 420 coincides with the known load of the master workpiece 200M (completion of the adjustment of a height of the load cell 420);

(5) lower the load cell 420 and also lower the workpiece clamp 400 to release the master workpiece 200M;

(6) fix the suspension 200, which is the object of measurement, on the reference plane 401 with the workpiece clamp 400;

(7) lift the load cell 420 to bring it into abutment against the ascending-end stopper 430 which has been adjusted in (4) above; and (8) obtain a load outputted by the load cell 420 in the state of (7) as a head load of the suspension 200.

However, the conventional technique does not give accurate results. In particular, in a suspension that supports a magnetic head, accuracy required in measurement of a head load is extremely high. Whereas a load required of the suspension was about 3±1.5 grams-force (gf) or 2.5±0.4 gf in the past, the load is measured at accuracy of as high as, for example, 0.4±0.04 gf recently.

SUMMARY OF THE INVENTION

It is an object of the present invention to increase the accuracy of measurement of the load on the spring.

A method according to an aspect of the present invention is a method of measuring load on a spring, the spring having a fixed end and a free end, a specific portion of the free end is elevated from the fixed end, and a load measuring device that measures the load on the spring is arranged so as to make a physical contact with the free end. The method includes measuring an elevation from the fixed end of a specific portion of the load measuring device where the free end and the load measuring device make the physical contact with each other; determining whether the elevation measured is equal to a specific elevation; and measuring the load on the spring with the load measuring device when it is determined at the determining that the elevation measured is equal to a specific elevation.

A method according to another aspect of the present invention is a method of measuring load on a spring, the spring having a fixed end and a free end, a specific portion of the free end is elevated from the fixed end, and a load measuring device that measures the load on the spring is arranged so as to make a physical contact with the free end. The method includes measuring an elevation from the fixed end of a specific portion of the free end where the free end and the load measuring device make the physical contact with each other; determining whether the elevation measured is equal to a specific elevation; and measuring the load on the spring with the load measuring device when it is determined at the determining that the elevation measured is equal to a specific elevation.

A method according to still another aspect of the present invention is a method of measuring load on a spring, the spring having a fixed end and a free end, the free end is elevated from the fixed end, and a load measuring device that measures the load on the spring is arranged so as to make a physical contact with the free end. The method includes calculating a spring constant of the spring; determining whether the free end is elevated from the fixed end to a specific elevation; and measuring the load on the spring with the load measuring device when it is determined at the determining that the free end is elevated from the fixed end to the specific elevation.

A device according to still another aspect of the present invention is a device for measuring load on a spring, the spring having a fixed end and a free end, a specific portion of the free end is elevated from the fixed end, and a load measuring device that measures the load on the spring is arranged so as to make a physical contact with the free end. The device includes a measuring/determining unit that measures an elevation from the fixed end of a specific portion of the load measuring device where the free end and the load measuring device make the physical contact with each other, and determines whether the elevation measured is equal to a specific elevation. The load measuring device is caused to measure the load on the spring when it is determined by the measuring/determining unit that the elevation measured is equal to a specific elevation.

A system according to still another aspect of the present invention is a system for measuring load on a spring, the spring having a fixed end and a free end, a specific portion of the free end is elevated from the fixed end. The system includes a load measuring device that measures the load on the spring is arranged so as to directly or indirectly make a physical contact with the free end; and a measuring/determining unit that measures an elevation from the fixed end of a specific portion of the load measuring device where the free end and the load measuring device make the physical contact with each other, and determines whether the elevation measured is equal to a specific elevation. The load measuring device is caused to measure the load on the spring when it is determined by the measuring/determining unit that the elevation measured is equal to a specific elevation.

The other objects, features, and advantages of the present invention are specifically set forth in or will become apparent from the following detailed description of the invention when read in conjunction with the accompanying drawings.

DETAILED DESCRIPTION

Exemplary embodiments of the present invention will be hereinafter explained in detail with reference to the accompanying drawings. Note that the present invention is not limited by the embodiments.

First, a premise leading to the embodiments will be explained.

Figure 9:
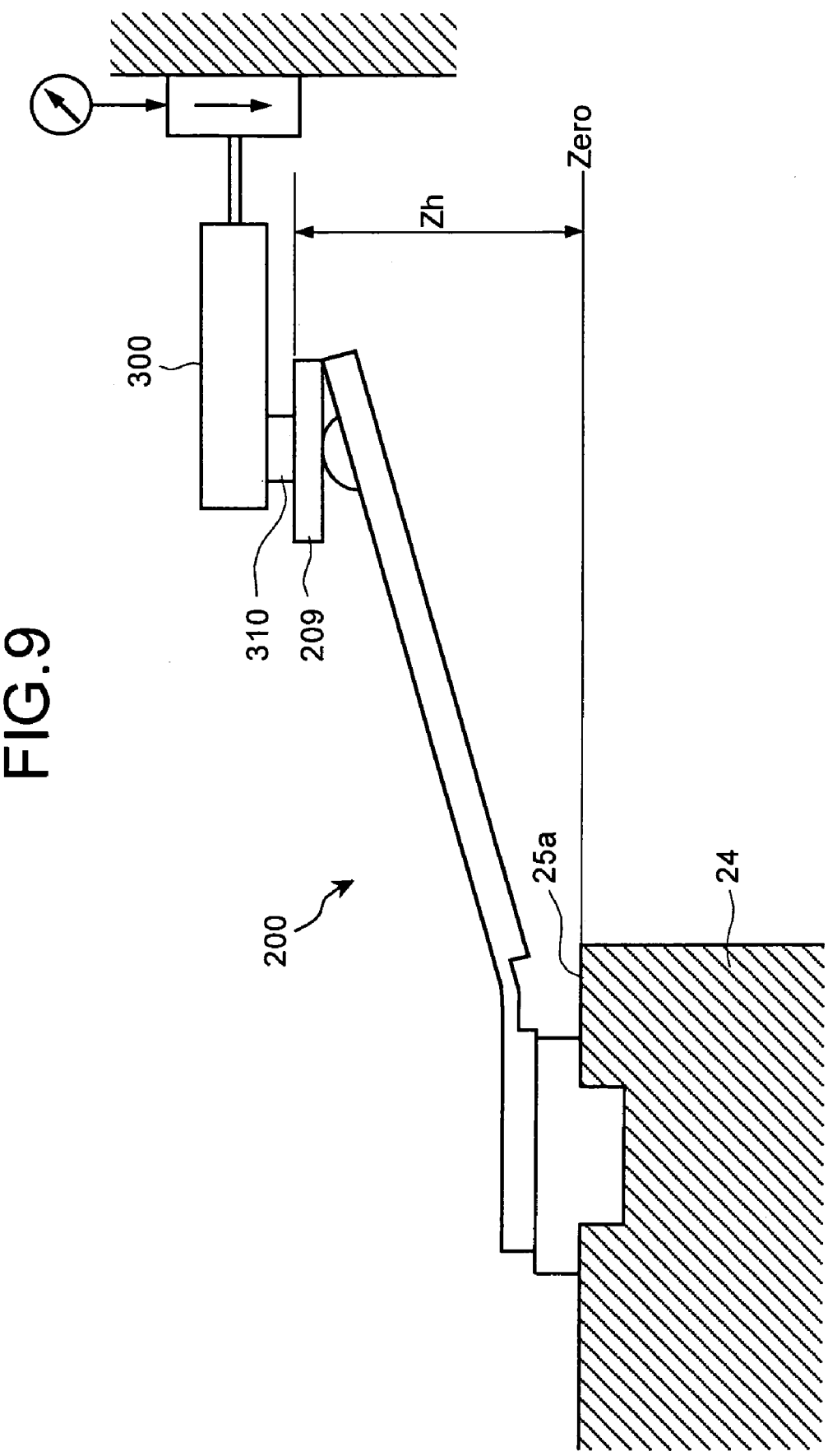
FIG. 9 is a side view showing a conventional method of measuring a head load of a suspension.

Accurate measurement cannot be performed with a conventional spring load measurement method shown in FIG. 9. This will be explained with reference to FIG. 1.

Conventionally, as shown in FIG. 9, in measuring a head load of a suspension 200, in a state in which a load probe 310 of a load cell 300 is in contact with a flexure 209, the load cell 300 is lowered to depress the flexure 209 to a position of a height Zh and measure a load from the flexure 209 in that state with the load cell 300.

Figure 1:
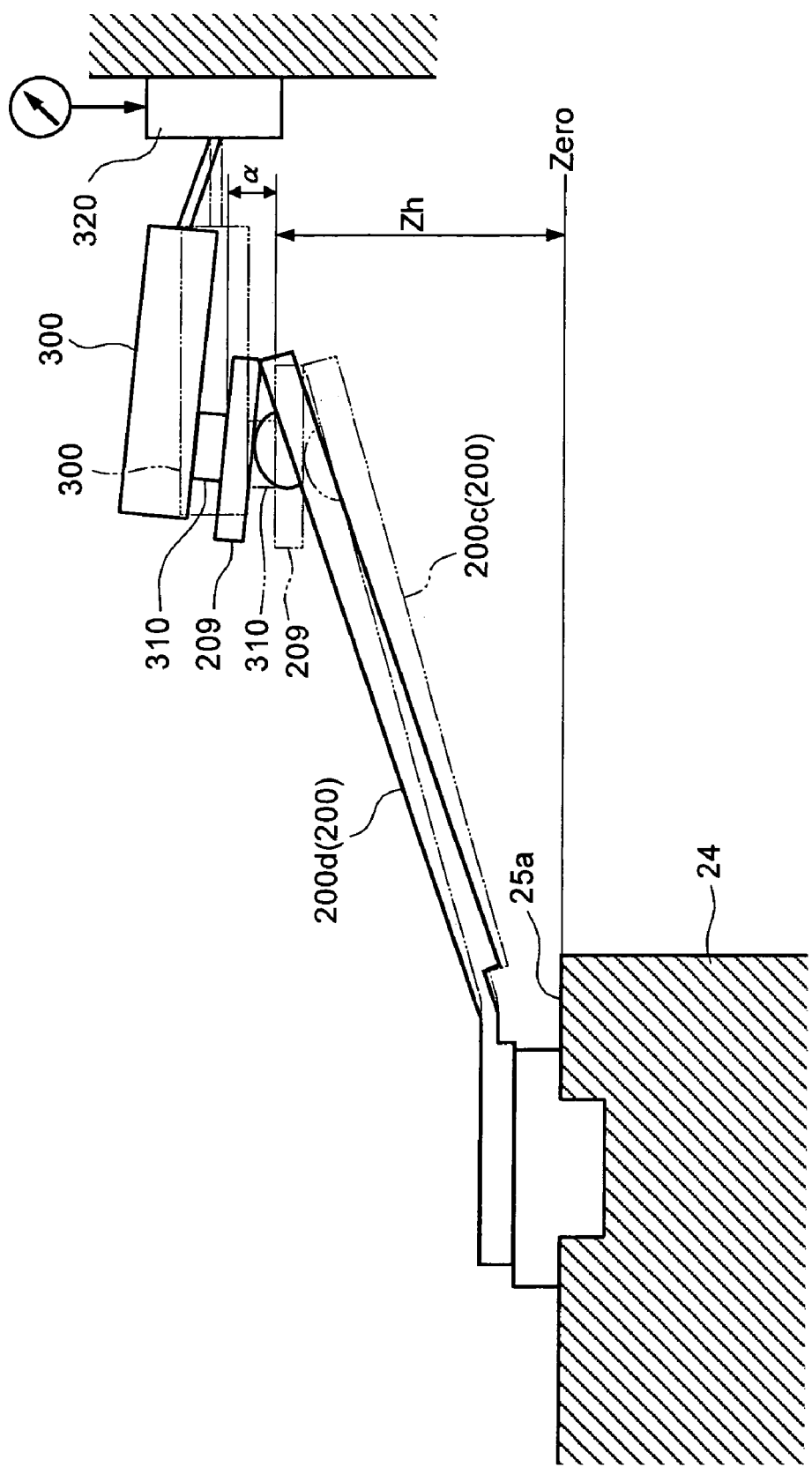
FIG. 1 is a side view for explaining the method of measuring the load on a spring according to an embodiment of the present invention.

However, in actual measurement, as shown in FIG. 1, a tip of the load cell 300 (the part of the load probe 310) is subject to a load from the flexure 209 and bends, and the flexure further separates from a reference plane 25*a* by α equivalent to an amount of the bending. In the above description, when the flexure 209 is depressed to the position of the height Zh, conventionally, an amount of depression of the flexure 209 (height of the load cell 300) is determined based on a height of a housing 320 of the load cell.

Since the amount of depression is determined based on the height of the housing 320 of the load cell 300 in this way, the bending of the tip of the load cell 300 is not taken into account. Consequently, the load cell 300 actually measures a load at a height of (Zh+α) from the reference plane 25*a*, and a load smaller than an actual load at the height Zh, at which it is truly desired to measure a load, is outputted.

In addition, the suspension 200 has a tolerance of the height Zf at the time when it is free, a tolerance of a length in a longitudinal direction, and the like. The amount of bending α at the tip of the load cell 300 varies depending on the suspension 200 and affects the height of the flexure 209 differently.

Therefore, accurate measurement cannot be performed with the conventional method.

This will be hereinafter verified using specific numerical values.

A suspension with 2.5 grams-force is measured using a load cell with a rated capacity of 10 grams-force and a rated displacement amount of ±0.4 millimeters (mm). Note that a spring constant of the suspension is assumed to be 2.3 gf/mm. When a suspension with 2.7 grams-force is measured in this setting, the following relation is obtained:

$$0.4:10=X:(2.7-2.5)$$

where X is 0.008 (a tip of the load cell bends away from the suspension by 0.008 mm).

This is converted into a load as follows:

$$P=0.008\times2.3=0.018 \text{ gf}$$

A load to be outputted by the load cell is smaller than an actual load by about 0.02 gf.

Some suspensions have a load tolerance of ±0.04 gf. In this case, practical measurement cannot be performed.

The tip of the load cell 300 is subjected to the load of the spring and bends as described above, whereby accurate measurement for the spring is prevented. Thus, it is conceivable to measure a load of the spring accurately using a load cell having a tip that does not easily bend (with less bending).

However, when the same suspension 200 is measured using a load cell with a characteristic of small bending and a load cell with a characteristic of large bending, an output level of the load cell with the characteristic of small bending is smaller than an output level of the load cell with the characteristic of large bending. Since the output level is small in the load cell with the characteristic of small bending, there is only a small difference between an output level at the time when no load is applied to the load cell and an output level at the time when a load is applied to the load cell. When the difference in the output level is small, the load cell is easily affected by noise (has a low SN ratio) and cannot measure a load accurately.

As described above, an amount of bending and the SN ratio are in a relation of tradeoff. Therefore, a method of measuring a spring load, with which a load can be measured accurately, is required even if a load cell has a large amount of bending.

Figure 2:
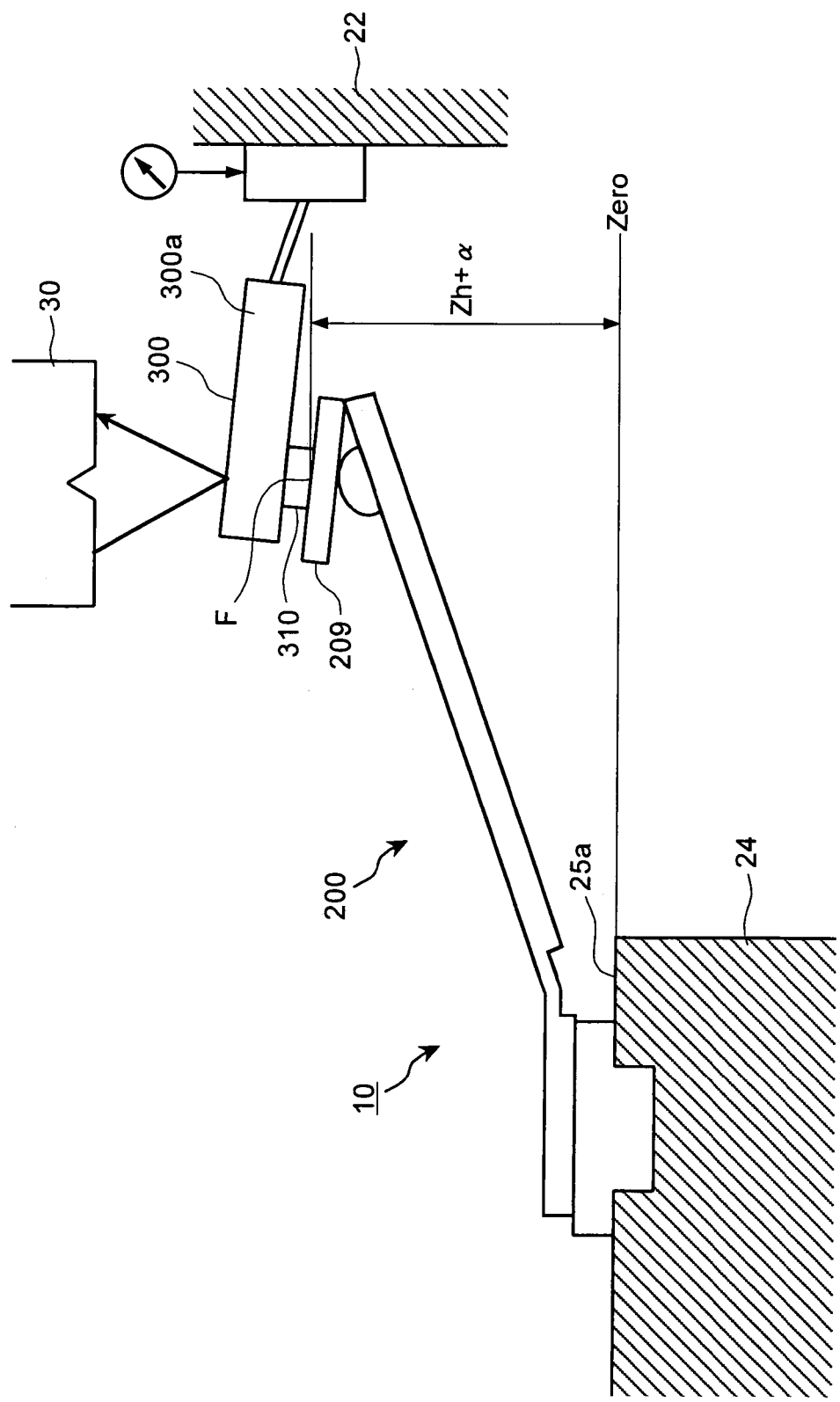
FIG. 2 is another side view for explaining the method of measuring the load on a spring according to an embodiment of the present invention.

FIG. 2 is a side for explaining a spring load measurement method according to a first embodiment of the present invention.

As shown in FIG. 2, a workpiece clamp unit 10, which clamps a suspension 200 that is an object of measurement, a load cell 300, which is capable of moving up and down along a column 22, and a measurement unit 30, which measures a height of a tip of the load cell 300 (the part of a load probe 310), are provided. Note that, in this embodiment, the load cell 300 is used as an example of a load measurement device. However, a load measurement device of the present invention is not limited to the load cell 300.

This measurement unit 30 is preferably a non-contact type displacement gauge such as a laser that can perform the measurement even if the height or the load of the object changes. A position of this measurement unit 30 is fixed. When the height of the tip of the load cell 300 changes, for example, a laser beam is irradiated from the laser displacement gauge 30, and a position where reflection of the laser beam (a return position, a return angle, etc.) changes. The measurement unit 30 detects the height of the tip of the load cell 300 according to the change in the position.

In this embodiment, a height of a flexure 209 including an amount of bending (α) (Zh+α) is calculated. In this case, a measurement position is a pressurization point F where the flexure 209 pressurizes the load cell 300.

Thicknesses of the load probe 310 and a load cell body 300a are fixed. Thus, when a laser beam is irradiated on an upper surface of the load cell body 300a (right above the pressurization point F where the flexure 209 pressurizes the load cell 300), the height (Zh+α) of the flexure 209 can be calculated based on a position where reflection of the laser beam is received.

Next, a height of the load cell 300 is adjusted (in this case, the load cell 300 is lowered) based on the height of the tip of the load cell 300 detected by the laser displacement gauge 30 to set a height of the flexure 209 (the pressurizing point F where the flexure 209 pressurizes the load cell 300) to Zh. If an output (load) of the load cell 300 is calculated at that point, a head load of the suspension 200 can be calculated.

Note that a portion, where a height is detected by the laser displacement gauges 30, may be a portion of a suspension 200 instead of the tip of the load cell 300. In this case, a height near a portion, with which the load probe 310 of the flexure 209 is in contact, can be calculated by the laser displacement gauge 30. The height of the load cell 300 is adjusted (in this case, lowered) based on the height of the flexure 209 detected by the laser displacement gauge 30 to set the height of the flexure 209 (the pressurizing point F where the flexure 209 pressurizes the load cell 300) to Zh. If an output (load) of the load cell 300 at that point is calculated, a head load of the suspension 200 can be calculated.

With the conventional measurement method, since it is necessary to reduce bending (an amount of clearance) of the tip of the load cell 300 to control a measurement error, it is necessary to use a load cell with a characteristic of minimum bending. Thus, the load cell has a low output voltage and is susceptible to noise in measurement of a very small load.

On the other hand, in this embodiment, the height of the pressurizing point F, where the flexure 209 pressurizes the load cell 300 (the height Zh+α at F at the time when the tip of the load cell 300 bends) is measured. This makes it possible to use a load cell with a characteristic of large bending and increases a degree of freedom of design or selection of a load cell. As a result, accurate measurement resistant to noise can be performed.

A second embodiment of the present invention will be explained with reference to FIGS. 3 to 6.

Figure 6:
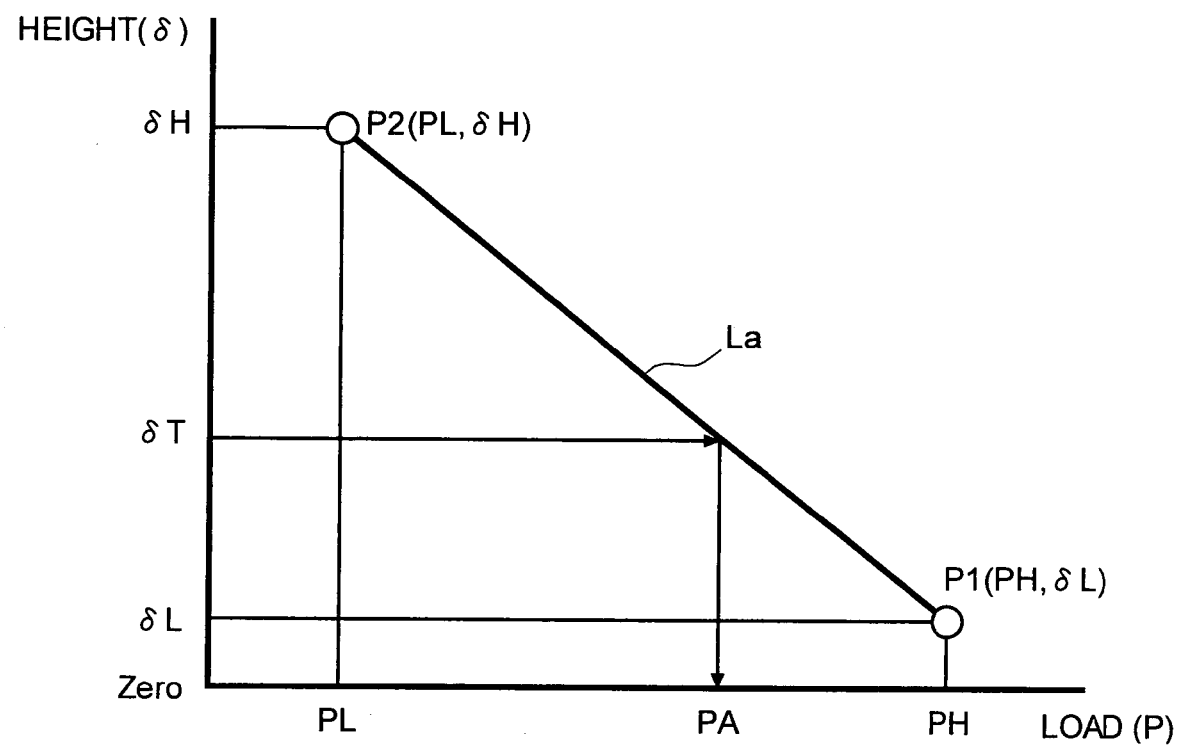
FIG. 6 is a graph showing a load-height diagram used in the spring load measurement method according to the embodiment.

Loads (PH and PL) are measured at heights (δH and δL) at two points above and below a target height (δT) in product design corresponding to a height at which a head load should be measured. In that case, since a tip of a load cell 300 bends away from a suspension 200 due to a reaction of a load, a height of the tip is measured. A load-height (bending) diagram of the suspension 200, which is an object of measurement, is prepared from the measured heights at two points (FIG. 6). The target height (δT) is inputted in this diagram to calculate a load (PA) at that height (δT) and set the load as a measurement value. Consequently, displacement of a portion to be deformed is measured directly such that an error due to the bending (deformation) of the tip of the load cell 300 does not occur, whereby the deformation does not affect the measurement of the height. This will be hereinafter explained more specifically.

In the second embodiment, a height of the tip of the load cell 300 is measured using a laser displacement gauge 30 as in the first embodiment.

In the second embodiment, sets of a load and a height at a pressurizing point, where the flexure 209 pressurizes the load cell 300, are measured at two points of different heights to prepare a load-height (bending) diagram based on a result of the measurement. A load (heat load) at a predetermined height (height Zh for measuring a head load) is calculated based on this load-height diagram. This calculated load at the predetermined height is an accurate value with bending (clearance) of the tip of the load cell 300 cancelled.

A procedure for adjusting the origin will now be explained in detail.

Figure 3:
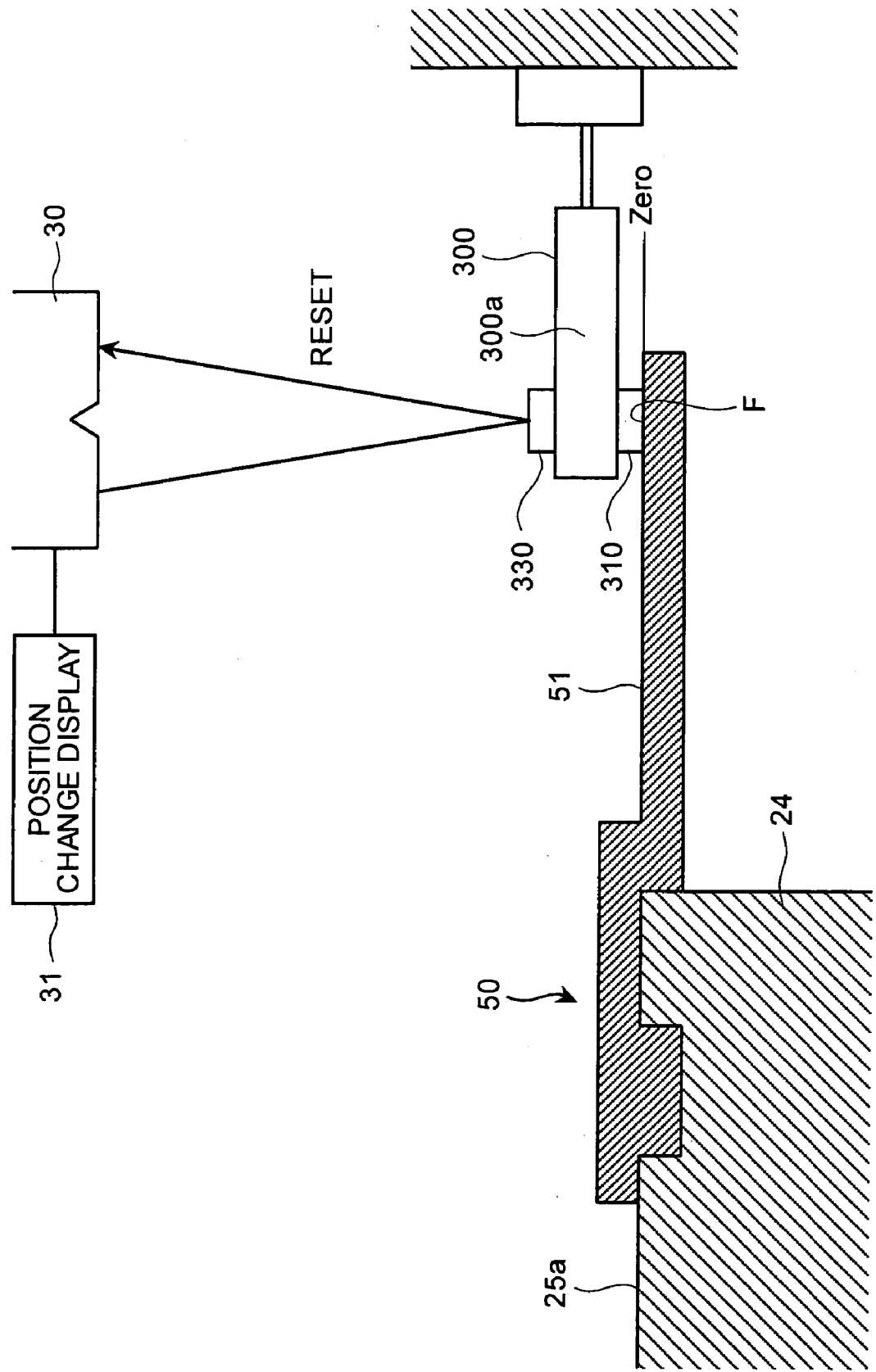
FIG. 3 is a side view showing a step of a spring load measurement method according to an embodiment of the present invention.

As shown in FIG. 3, a zero adjustment gauge 50 is set on a support 24. The zero adjustment gauge 50 is constituted to have a surface 51 that is at the same height as a reference surface 25a when the zero adjustment gauge 50 is set on the support 24.

The height of the load cell 300 is adjusted to bring a load probe 310 of the load cell 300 into contact with the surface 51 of the zero adjustment gauge 50.

Then, in a state in which the load probe 310 of the load cell 300 starts to come into contact with the surface 51 of the zero adjustment gauge 50, a laser beam is irradiated on a laser irradiated section 330 of the load cell 300 from the laser displacement gauge 30. A position of the laser irradiated section 330 obtained from reflection of the laser beam is recorded as a height zero point (reference point).

Here, the laser irradiated section 330 is a section that is provided at a position right above the load probe 310 of the load cell 300 and set as a target of laser irradiation to thereby measure a height of a pressurizing point F where the flexure 209 pressurizes the load cell 300 (load probe 310). Note that a thickness of the load probe 310, a thickness of the load cell body 300a, and a thickness of the laser irradiated section 330 are fixed. The height of the pressurizing point F where the flexure 209 pressurizes the load cell 300 can be calculated by deducting a total of the thickness of the load probe 310, the thickness of the load cell body 300a, and the thickness of the laser irradiated section 330 from the thickness of the laser irradiated section obtained by the laser displacement gauge 30.

Figure 4:
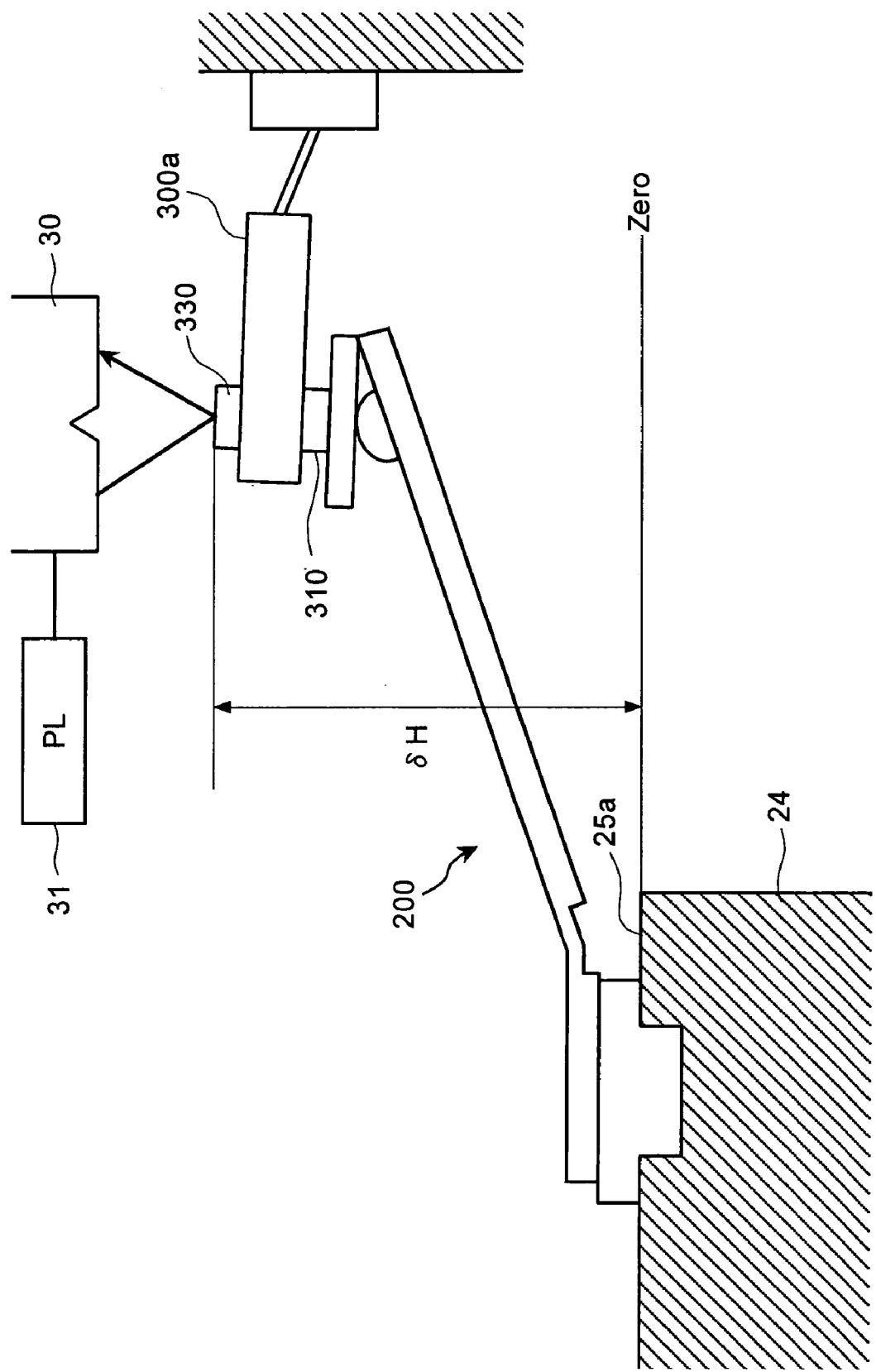
FIG. 4 is a side view showing another step of the spring load measurement method according to the embodiment.
Figure 5:
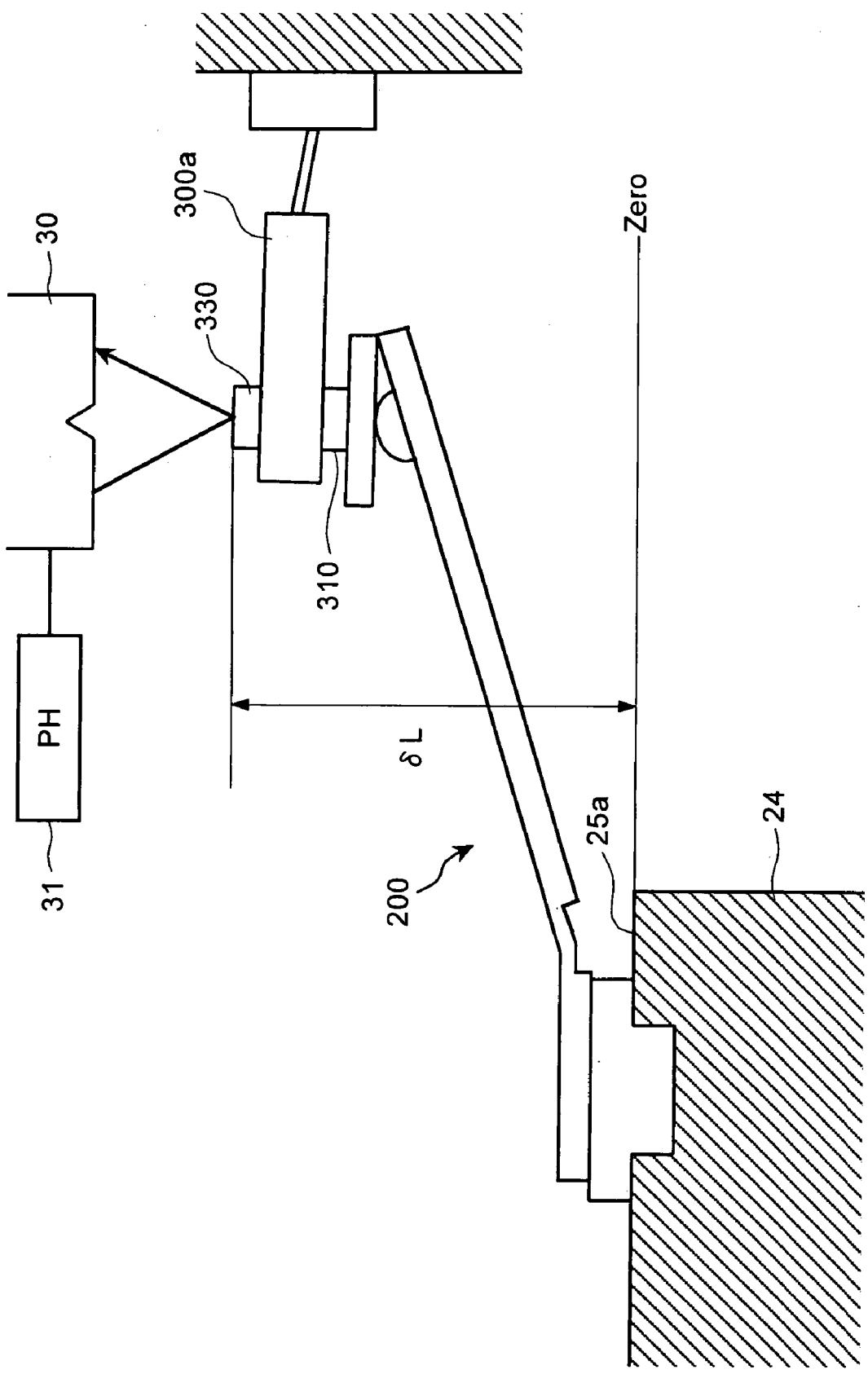
FIG. 5 is a side view showing yet another step of the spring load measurement method according to the embodiment.

Next, as shown in FIGS. 4 and 5, heights of the laser irradiated section 330 and loads on the suspension 200 are measured at two points of different heights, respectively. The height of the laser irradiated section 330 is higher than that shown in FIG. 5. The height of the laser irradiated section 330 and the load of the suspension 200 in FIG. 4 are assumed to be δH and PL, respectively. The height of the laser irradiated section 330 and the load of the suspension 200 in FIG. 5 are assumed to be δL and PH, respectively. These heights and loads are plotted on a load-height diagram as shown in FIG. 6.

As shown in FIG. 6, a straight line La is obtained when a point P2 that represents a result of measurement in FIG. 4 and a point P1 that represents a result of measurement in FIG. 5 are joined. This line La corresponds to a spring constant of the suspension. Here, a graph corresponding to the spring constant is obtained by connecting the two plots with a straight line.

Next, when a load at a predetermined height of the suspension 200 is to be obtained, a load P corresponding to δ according to the predetermined height only has to be calculated on the graph La shown in FIG. 6. Conversely, when a height at a predetermined load of the suspension 200 is to be obtained, a height δ corresponding to P according to the predetermined load only has to be calculated on the graph La shown in FIG. 6.

In obtaining a head load of the suspension 200, after setting the height δ to δT=(Zh+thickness of the load probe 310+thickness of the load cell body 300a+thickness of the laser irradiated section 330), a head load PA can be calculated from the graph La.

Next, when an object of measurement is changed to another suspension 200, heights of the laser irradiated section 330 and loads on the suspension 200 are measured at two points of different heights for the suspension 200 in the same manner as described above. Results of the measurement at the two points are plotted on a load-height diagram in the same manner as FIG. 6. Both the plots are connected to obtain a graph corresponding to a spring constant. A load at a predetermined height or a height at a predetermined load for the suspension 200 can be calculated based on the graph.

Note that a portion where a height is detected by the laser displacement gauge 30 may be a portion of the suspension 200 itself instead of a portion of the laser irradiated section 330. In this case, a height near a portion, with which the load probe 310 of the flexure 209 is in contact, can be calculated by the laser displacement gauge 30. Heights of the suspension 200 itself and loads on the suspension 200 are measured at two points of different heights, respectively. The heights of the suspension 200 itself is assumed to be δH and δL to prepare a load-height diagram. A load at the time when the suspension 200 is at a predetermined height can be calculated based on the load-height diagram.

According to the second embodiment, an accurate load with an amount of bending of the tip of the load cell 300 cancelled can be calculated.

In addition, since a spring constant of each spring (suspension 200) is measured, and then a load at a predetermined height is calculated, more accurate measurement can be performed.

Figure 7:
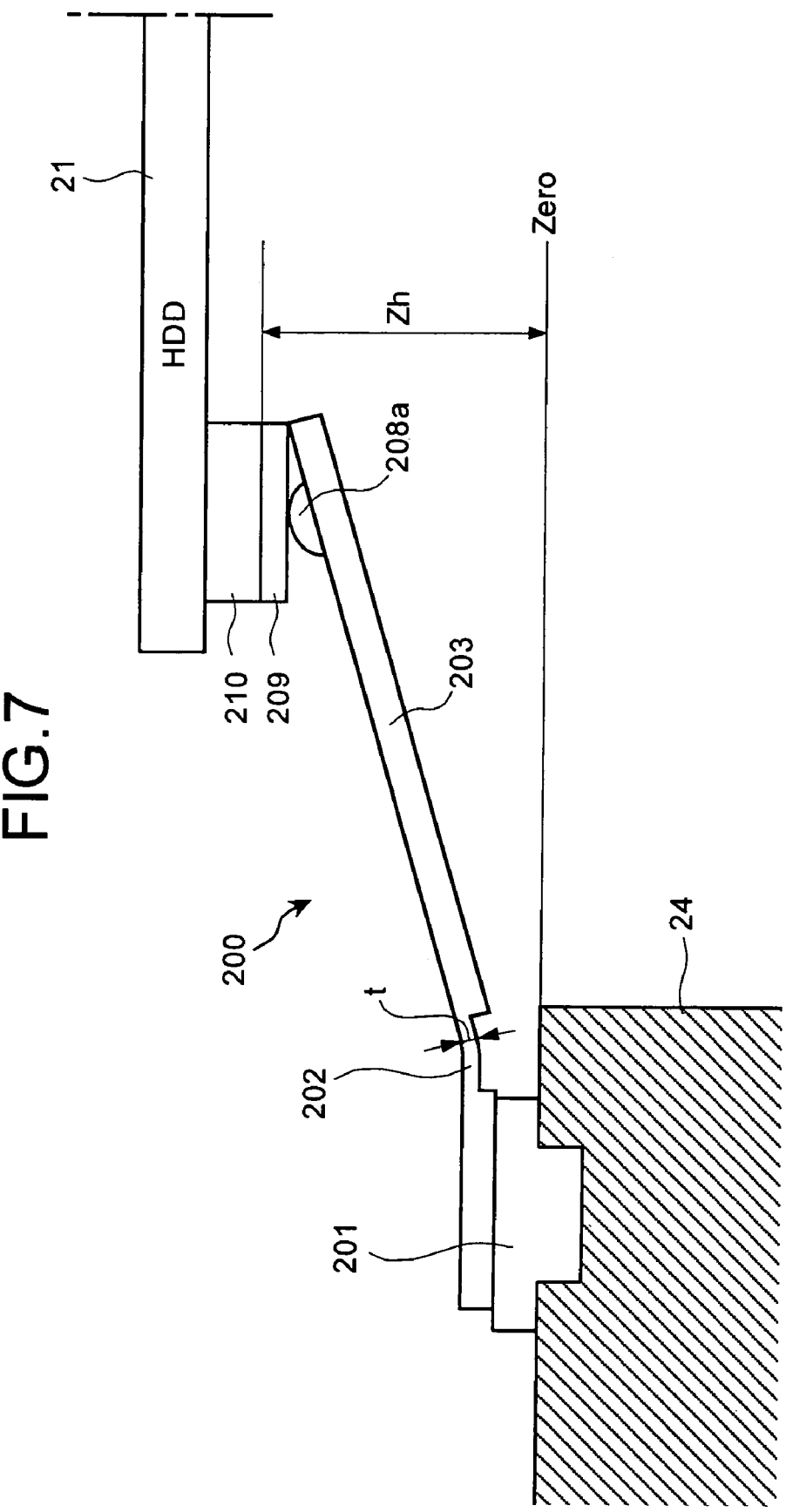
FIG. 7 is a side view showing a state of use of a conventional general suspension.
Figure 8:
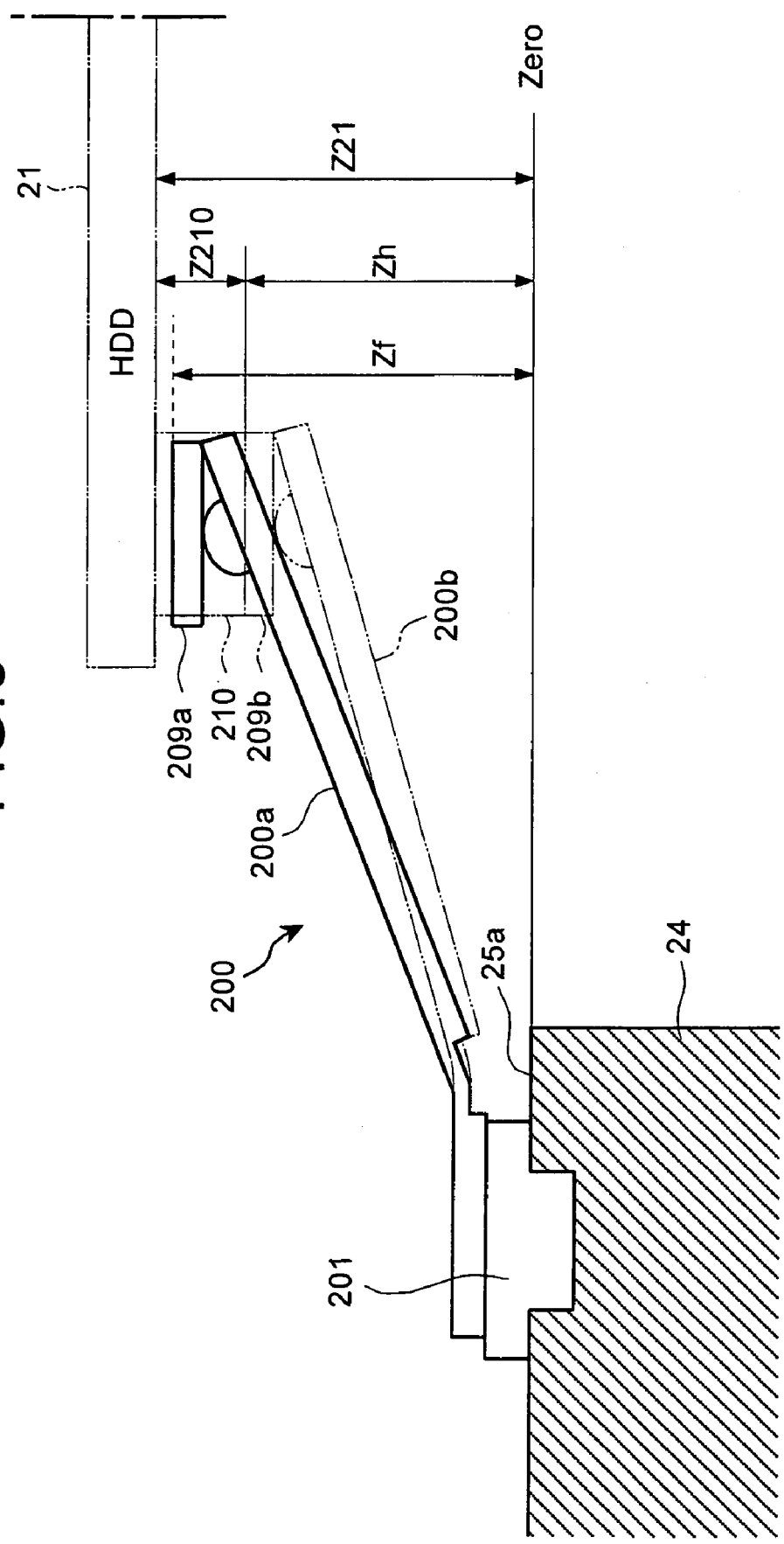
FIG. 8 is a side view showing a height at the time when the conventional general suspension is free.

For example, measurement of a load of the suspension for HDD (suspension) 200 will be described. In accordance with the improvement of a density of capacity in a HDD, load, which significantly affects reading and writing of signals, needs to be measured very accurately. A leaf spring section 202 (see FIG. 7) of this suspension 200 is formed by rolling or half etching. A thickness of the leaf spring section 202 (see "t" in FIG. 7) fluctuates by several percents in the rolling and several tens percents in the half etching. Thus, it is difficult to control the fluctuation within a load tolerance. On the other hand, in this embodiment, a spring constant is measured for each of the suspensions 200, which are objects of measurement, and then a load at a predetermined height or a height at a predetermined load for each of the suspensions 200 is calculated. This is effective for solving the problem of the fluctuation in the thickness of the leaf spring 202.

This embodiment is explained with the suspension 200 as an example. However, the present invention is not limited to this, and the above-mentioned effects can be realized for a spring in general.

Figure 10:
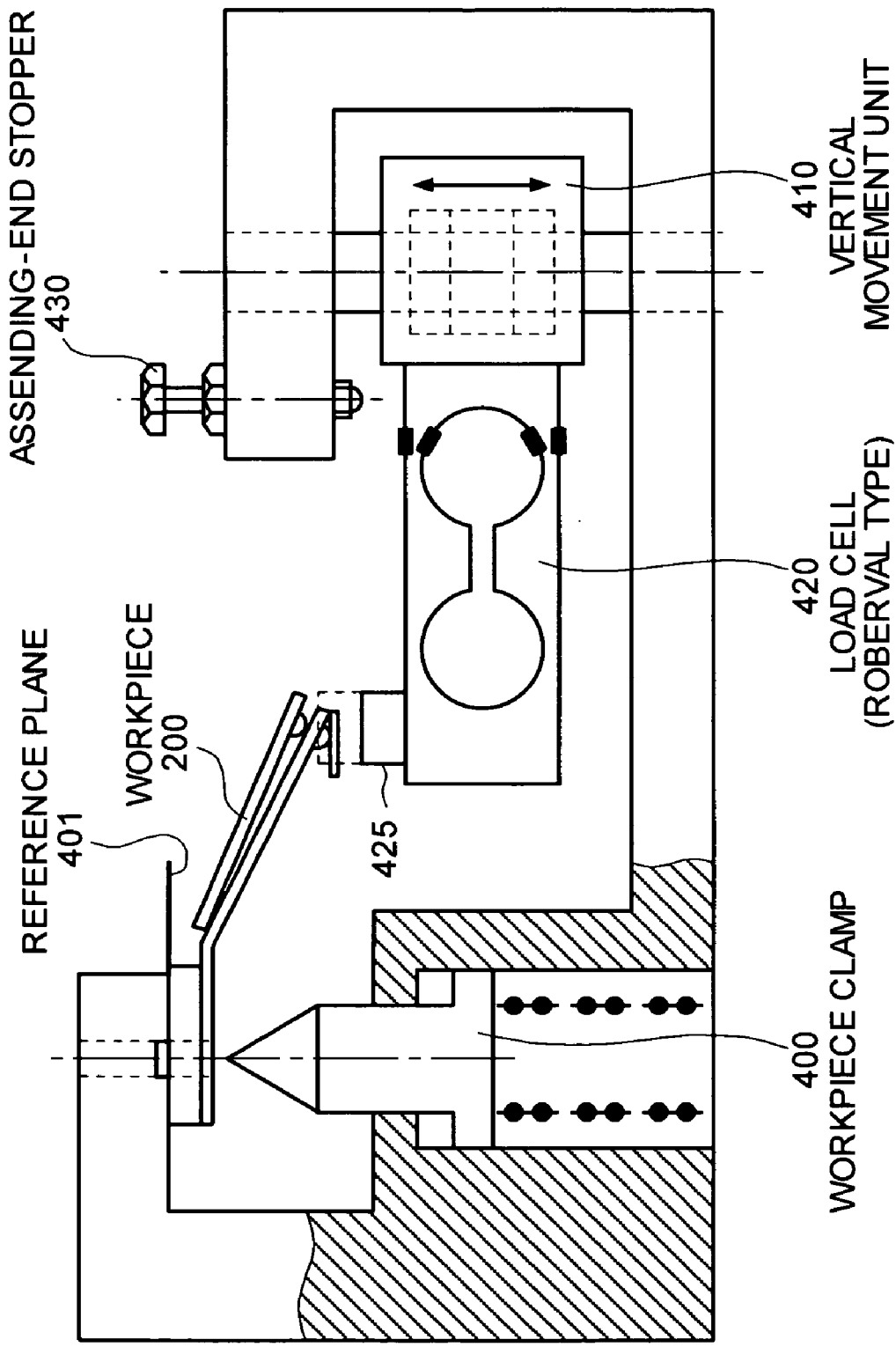
FIG. 10 is a side view showing another conventional method of measuring a head load of a suspension.

Conventionally, as shown in FIG. 10, a tip of a load cell 420 is brought into abutment against a measured section of a workpiece 200, and the workpiece 200 or the load cell 420 is moved to a predetermined height in a load generation direction to measure a load. In this case, the load cell 420 bends in a direction opposite to the workpiece 200 due to a reaction of the workpiece 200. As an example, when a load is 30 grams-force, the load cell 420 bends by 0.012 millimeters. As explained with reference to FIG. 10, usually, the predetermined height is determined in anticipation of this bending. Therefore, accurate measurement cannot be performed when a spring constant is different or when a load is different.

Moreover, according to the second embodiment, a very small load can be measured in very little time. This effect will be hereinafter explained. In measuring a very small load of a spring, it takes several seconds until vertical vibration of a measurement system subsides. This is because, since the number of vibration peculiar to the measurement system is low, amplitude hardly attenuates. On the other hand, in this embodiment, vertical vibration may remain as long as a height and a load at a certain point in time can be measured. In addition, in this embodiment, since loads and heights are measured at two points of different heights, a graph indicating an accurate spring constant can be obtained, which is advantageous in that more accurate measurement can be performed.

Note that, when an electronic balance system is used, it takes several seconds until a spring comes into a balanced state. Thus, the electronic balance system is not suitable for high-speed measurement.

In each of the first and the second embodiments, a head load is measured with respect to the suspension 200 not yet mounted with the slider 210. On the other hand, it is also possible to measure a head load with respect to the suspension 200 mounted with the slider 210 in each of the first and the second embodiments. As a measurement method in that case, all what should be performed is that, in the explanation of the first and the second embodiments, an object against which the load probe 310 of the load cell 300 is brought into abutment is changed from the flexure 209 to the slider 210 mounted on the flexure 209, and in utilizing a result of measurement of the laser displacement gauge 30, a thickness of the slider 210 is taken into account.

If a height of the tip of the load cell 300 is calculated in a state in which the slider 210 is attached, since a thickness involved in attachment of the slider 210 can be taken into account, a head load at the time when the slider 210 actually comes into contact with the magnetic disk 21 can be measured more accurately.

In the second embodiment in which heights and loads at two different points are calculated and a spring constant is fond from a height-load diagram, an object for which the heights are measured is the tip of the load cell 300. However, the object may be the housing 320 of the load cell 300 as in the conventional technique. Even in this case, since heights and loads of the housing 320 are measured at plural points to prepare a height-load diagram, more accurate load measurement can be performed compared with the conventional technique.

In accordance with an increase in a capacity of a HDD, a load of the suspension 200 has become smaller, moreover, the load needs to measured more accurately. Conventionally, the load cell 300 is used to measure the load; however, there was a problem that the measurement was inaccurate due to clearance of the load cell 300. On the contrary, according to the present invention, displacement of the load cell 300 is measured together with the load to prepare a load-bending diagram according to arithmetic operation processing and estimate a load at a predetermined height from the diagram. Therefore, the load on the spring can be measured more accurately so that the method can be used in manufacturing of improved springs.

Although the invention has been described with respect to a specific embodiment for a complete and clear disclosure, the appended claims are not to be thus limited but are to be construed as embodying all modifications and alternative constructions that may occur to one skilled in the art which fairly fall within the basic teaching herein set forth.

What is claimed is:

1. A method of measuring load on a spring, the spring having a fixed end and a free end, a specific portion of the free end is elevated from the fixed end, and a load measuring device that measures the load on the spring is arranged so as to make a physical contact with the free end, comprising:
   measuring an elevation from the fixed end to a specific portion of the load measuring device where the free end and the load measuring device make the physical contact with each other;
   determining whether the elevation measured is equal to a specific elevation; and
   measuring the load on the spring with the load measuring device when it is determined at the determining that the elevation measured is equal to a specific elevation.

2. The method according to claim 1,
   wherein the specific portion of the load measurement device is subjected to a load or a reaction from the spring and bends.

3. The method according to claim 1,
   wherein the specific portion corresponds to a position of a load probe for measuring a load of the spring.

4. The method according to claim 1,
   the measuring an elevation includes measuring the elevation from the fixed end of the specific portion by using a non-contact type displacement gauge.

5. The method according to claim 1, wherein
   the spring is a suspension that fixedly supports a magnetic head of a hard disk drive.

6. The method according to claim 5,
   wherein the load measurement device makes a physical contact with the suspension via the magnetic head.

7. A method of measuring load on a spring, the spring having a fixed end and a free end, a specific portion of the free end is elevated from the fixed end, and a load measuring device that measures the load on the spring is arranged so as to make a physical contact with the free end, comprising:
   measuring an elevation from the fixed end to a specific portion of the free end where the free end and the load measuring device make the physical contact with each other;
   determining whether the elevation measured is equal to a specific elevation; and
   measuring the load on the spring with the load measuring device when it is determined at the determining that the elevation measured is equal to a specific elevation.

8. The method according to claim 7,
   wherein the specific portion corresponds to a position of a load probe for measuring a load of the spring.

9. The method according to claim 7,
   the measuring an elevation includes measuring the elevation from the fixed end of the specific portion by using a non-contact type displacement gauge.

10. The method according to claim 7, wherein
    the spring is a suspension that fixedly supports a magnetic head of a hard disk drive.

11. The method according to claim 10,
wherein the load measurement device makes a physical contact with the suspension via the magnetic head.

12. A method of measuring load on a spring, the spring having a fixed end and a free end, the free end is elevated from the fixed end, and a load measuring device that measures the load on the spring is arranged so as to make a physical contact with the free end, comprising:
calculating a spring constant of the spring;
determining whether the free end is elevated from the fixed end to a specific elevation; and
measuring the load on the spring with the load measuring device when it is determined at the determining that the free end is elevated from the fixed end to the specific elevation,
wherein the calculating includes:
positioning the load measurement device in such a manner that the contact between the load measurement device and the free end of the spring is at a first elevation with respect to the fixed end, and measuring a load on the spring as a first load;
positioning the load measurement device in such a manner that the contact between the load measurement device and the free end of the spring is at a second elevation, which is different from the first elevation, with respect to the fixed end, and measuring a load on the spring as a second load; and
calculating the spring constant from the first elevation, the second elevation, the first load, and the second load.

13. A method of measuring load on a spring, the spring having a fixed end and a free end, the free end is elevated from the fixed end, and a load measuring device that measures the load on the spring is arranged so as to make a physical contact with the free end, comprising:
calculating a spring constant of the spring;
determining whether the free end is elevated from the fixed end to a specific elevation; and
measuring the load on the spring with the load measuring device when it is determined at the determining that the free end is elevated from the fixed end to the specific elevation,
wherein the calculating includes:
positioning the load measurement device in such a manner that the contact between the load measurement device and the free end of the spring is at a first elevation with respect to the fixed end, measuring a load on the spring as a first load, and measuring an elevation from the fixed end to a specific portion of the load measurement device as a third elevation;
positioning the load measurement device in such a manner that the contact between the load measurement device and the free end of the spring is at a second elevation, which is different from the first elevation, with respect to the fixed end, measuring a load on the spring as a second load, and measuring an elevation from the fixed end of the specific portion of the load measurement device as a fourth elevation; and
calculating the spring constant from the third elevation, the fourth elevation, the first load, and the second load.

14. The method according to claim 12, wherein
the first elevation is higher than a total of the specific elevation and a height of the load measurement device, and
the second elevation is lower than the total of the specific elevation and a height of the load measurement device.

15. The method according to claim 13, wherein
the first elevation is higher than a total of the specific elevation and a height of the load measurement device, and
the second elevation is lower than the total of the specific elevation and a height of the load measurement device.

16. A method of measuring load on a spring, the spring having a fixed end and a free end, the free end is elevated from the fixed end, and a load measuring device that measures the load on the spring is arranged so as to make a physical contact with the free end, comprising:
calculating a spring constant of the spring;
determining whether the free end is elevated from the fixed end to a specific elevation; and
measuring the load on the spring with the load measuring device when it is determined at the determining that the free end is elevated from the fixed end to the specific elevation,
wherein the calculating includes
positioning the free end of the spring in such a manner that the contact between the free end and the load measurement device is at a first elevation with respect to the fixed end, and measuring a load on the spring as a first load;
positioning the free end of the spring in such a manner that the contact between the free end and the load measurement device is at a second elevation, which is different from the first elevation, with respect to the fixed end, and measuring a load on the spring as a second load; and
calculating the spring constant from the first elevation, the second elevation, the first load, and the second load.

17. The method according to claim 16, wherein
the first elevation is higher than the specific elevation, and
the second elevation is lower than the specific elevation.

18. The method according to claim 12, wherein the spring is a suspension that fixedly supports a magnetic head of a hard disk drive.

19. The method according to claim 18,
wherein the load measurement device makes a physical contact with the suspension via the magnetic head.

20. A device for measuring load on a spring, the spring having a fixed end and a free end, a specific portion of the free end is elevated from the fixed end, and a load measuring device that measures the load on the spring is arranged so as to make a physical contact with the free end, comprising:
a measuring/determining unit that measures an elevation from the fixed end to a specific portion of the load measuring device where the free end and the load measuring device make the physical contact with each other, and determines whether the elevation measured is equal to a specific elevation, wherein
the load measuring device is caused to measure the load on the spring when it is determined by the measuring/determining unit that the elevation measured is equal to a specific elevation.

21. A system for measuring load on a spring, the spring having a fixed end and a free end, a specific portion of the free end is elevated from the fixed end, comprising:
a load measuring device that measures the load on the spring is arranged so as to directly or indirectly make a physical contact with the free end; and a measuring/determining unit that measures an elevation from the fixed end to a specific portion of the load measuring device where the free end and the load measuring device make the physical contact with each other, and determines whether the elevation measured is equal to a specific elevation, wherein the load measuring device is caused to measure the load on the spring when it is determined by the measuring/determining unit that the elevation measured is equal to a specific elevation.

22. The method according to claim 13, wherein the spring is a suspension that fixedly supports a magnetic head of a hard disk drive.

23. The method according to claim 14, wherein the spring is a suspension that fixedly supports a magnetic head of a hard disk drive.

* * * * *